(12) United States Patent  
Vashi

(10) Patent No.: US 8,938,838 B2  
(45) Date of Patent: Jan. 27, 2015

(54) TOOTHBRUSH WITH AN IMAGING DEVICE BEING CAMERA

(76) Inventor: Nikhil Shankarlal Vashi, Maharashtra (IN)

( * ) Notice: Subject to any disclaimer, the term of this patent is extended or adjusted under 35 U.S.C. 154(b) by 95 days.

(21) Appl. No.: 13/280,492

(22) Filed: Oct. 25, 2011

(65) Prior Publication Data

US 2013/0061412 A1    Mar. 14, 2013

(30) Foreign Application Priority Data

Sep. 12, 2011   (IN) .......................... 2558/MUM/2011

(51) Int. Cl.
- *A61C 17/00* (2006.01)
- *A46B 7/04* (2006.01)
- *A61B 5/00* (2006.01)

(52) U.S. Cl.
CPC ............... *A61B 5/0088* (2013.01); *A46B 7/042* (2013.01)
USPC .............................................. 15/22.1; 15/106

(58) Field of Classification Search
USPC ........................................... 15/106, 22.1, 23
See application file for complete search history.

(56) References Cited

U.S. PATENT DOCUMENTS

| 4,654,922 | A * | 4/1987 | Chen | 15/172 |
| 6,960,170 | B2 * | 11/2005 | Kuo | 600/551 |
| 2003/0221270 | A1 * | 12/2003 | Kuo | 15/29 |
| 2005/0177961 | A1 * | 8/2005 | Prineppi | 15/22.1 |

FOREIGN PATENT DOCUMENTS

| JP | 2001218624 A * | 8/2001 |
| JP | 2011194181 A * | 10/2011 |

* cited by examiner

*Primary Examiner* — Shay Karls  
(74) *Attorney, Agent, or Firm* — Excellere IP International; Anne Burkhart

(57) ABSTRACT

A toothbrush that contains an imaging device being camera for seeing teeth on an image display monitor before, during and after cleaning them and for storing and transferring images and videos of teeth and oral tissues for better maintenance of oral hygiene and health. The toothbrush with camera comprises a brush head (1) with bristles (3) and a camera (4), and a hollow handle (2) containing camera assembly. Different embodiments of the toothbrush with camera are disclosed herein.

16 Claims, 16 Drawing Sheets

TOOTHBRUSH WITH AN IMAGING DEVICE BEING CAMERA

TECHNICAL FIELD

The disclosure herein relates to a toothbrush that includes an imaging device being camera.

BACKGROUND OF THE INVENTION

Toothbrushes are used by people every day to clean their teeth by removing food remnants and dental plaque sticking on to the teeth. Dental plaque contains many bacteria that cause diseases of teeth and gums like dental caries, gingivitis, periodontitis etc. When plaque is not removed from the surfaces of teeth it turns into calculus also known as tartar. Calculus cannot be removed by normal brushing as it is hard and sticks to the teeth firmly. Progression of dental diseases may lead to loss of teeth over a period of time if not treated by a dentist. Unhealthy teeth and gums have adverse effects on the general health also.

Even though many varieties of toothbrushes are available in the markets, mainly two types of brushes are available, manual and motorised. Manual toothbrushes have rows of bristles placed on the brush head that is attached to a handle. FIG. 1 shows a manual toothbrush. Motorised toothbrushes have bristles mounted on a head in a circular arrangement. The head is attached to a handle that contains the motor for moving the head. The head rotates or oscillates in a semi-circle when started. FIG. 2 shows a motorised toothbrush.

A person brushing teeth is not able to see clearly the food and plaque deposits on the rear side of the front teeth and on the teeth that are in the back side of the mouth. So it is not possible for the person to determine whether the brushing is effective in cleaning the teeth thoroughly.

A person is not able to see if there is dental caries in the back teeth or swelling in the gums around the back teeth. Only a dentist would be able to tell the person during a regular dental check up if there is any dental disease present in the mouth.

These problems presented due to inability to see the teeth clearly in the mouth are overcome by a toothbrush with an imaging device being camera. So far no attempts have been made to develop such a toothbrush.

SUMMARY

In accordance with the principles herein, a toothbrush with a camera is set forth. The toothbrush with camera can be used for efficiently brushing teeth to maintain good oral hygiene and for detecting dental diseases easily. The toothbrush with camera can be used for sending images and videos of a person's teeth and mouth to a dentist's office for a consultation. The toothbrush with camera is very easy to manufacture and easy to operate.

A toothbrush constructed in accordance with the principles herein has several novel aspects. In general, the toothbrush includes a head attached to a handle. The head has tufts of bristles arranged in rows. A camera lens is placed in the head to capture pictures and videos to transmit to a display unit. A light source can be placed near the camera lens to illuminate the field of the camera. The handle contains the camera body and a power source for operating the camera and the light source. The handle has a switch to put on and put off the camera and the light and to record and transmit images and videos to a display unit with or without a cable.

Although many different embodiments of the toothbrush with a camera are described, the toothbrush with camera essentially works in the same manner in all the embodiments.

The objects and advantages of the toothbrush with camera herein will become apparent from a consideration of the drawings and ensuing description.

DETAILED DESCRIPTION

The following describes exemplary embodiments constructed in accordance with the principles herein as illustrated in FIGS. 3 to 34.

Figure 1:
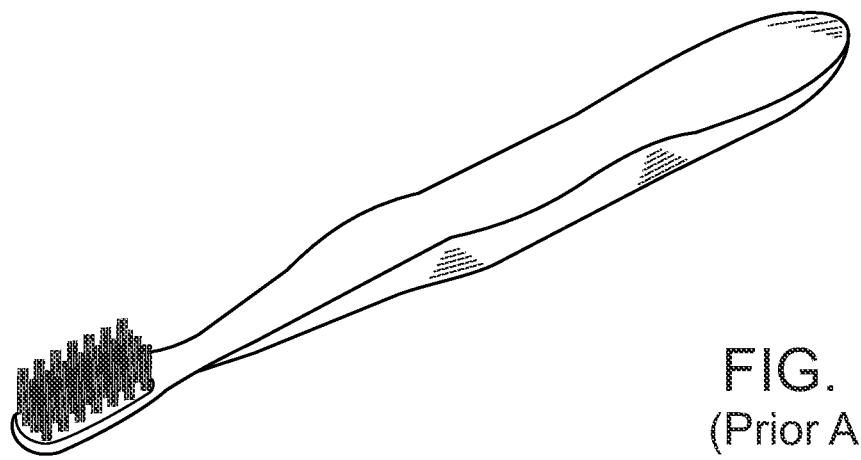
FIG. 1 is a perspective view of a typical prior art manual toothbrush.
Figure 2:
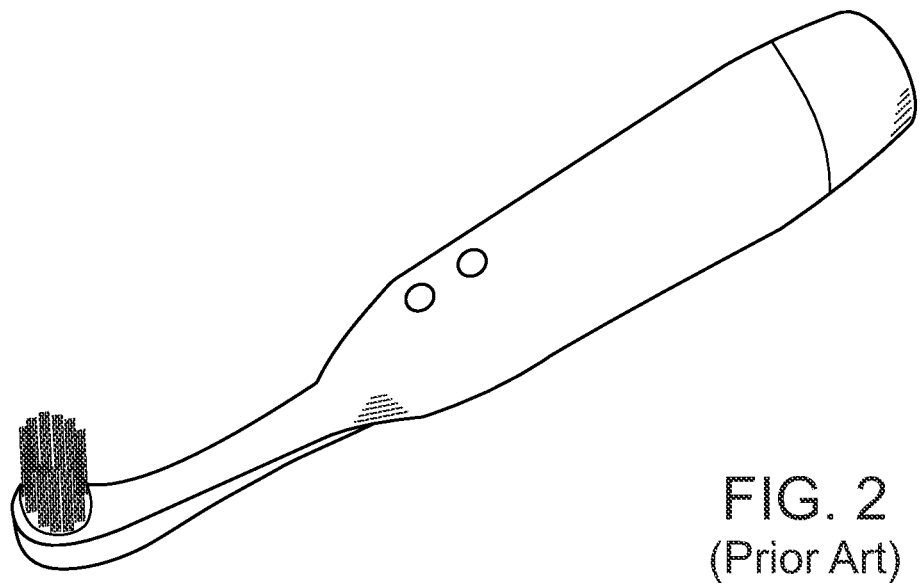
FIG. 2 is a perspective view of a typical prior art motorised toothbrush.
Figure 3:
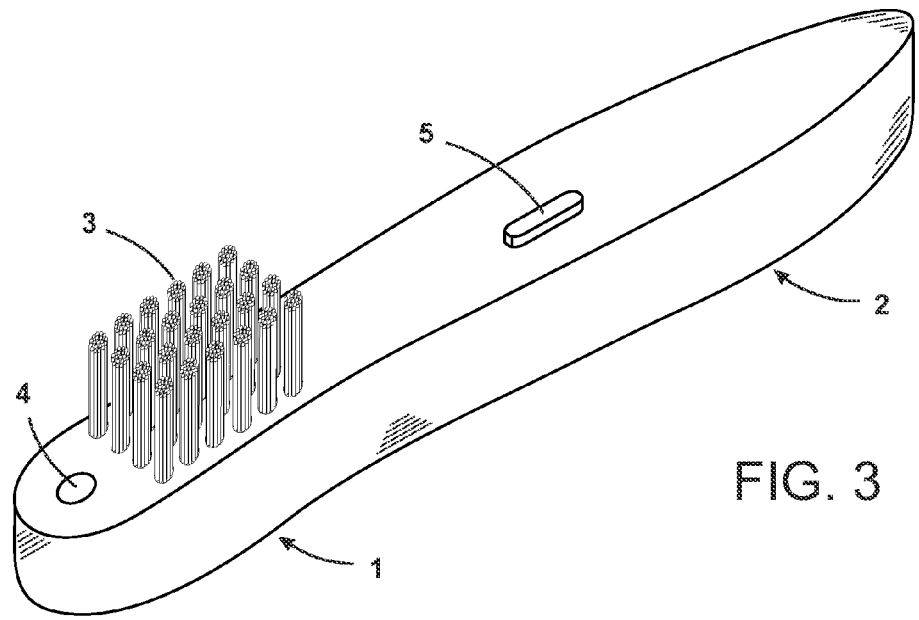
FIG. 3 is a perspective view of one embodiment of a toothbrush with camera according to the present invention.
Figure 4:
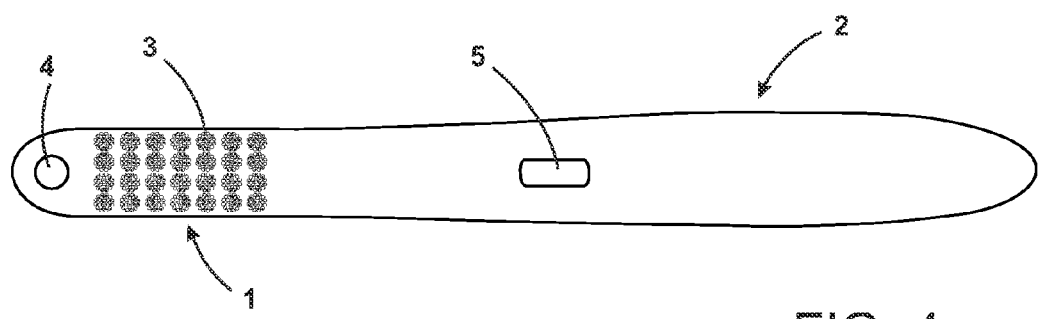
FIG. 4 is a top view of the toothbrush with camera of FIG. 3.
Figure 5:
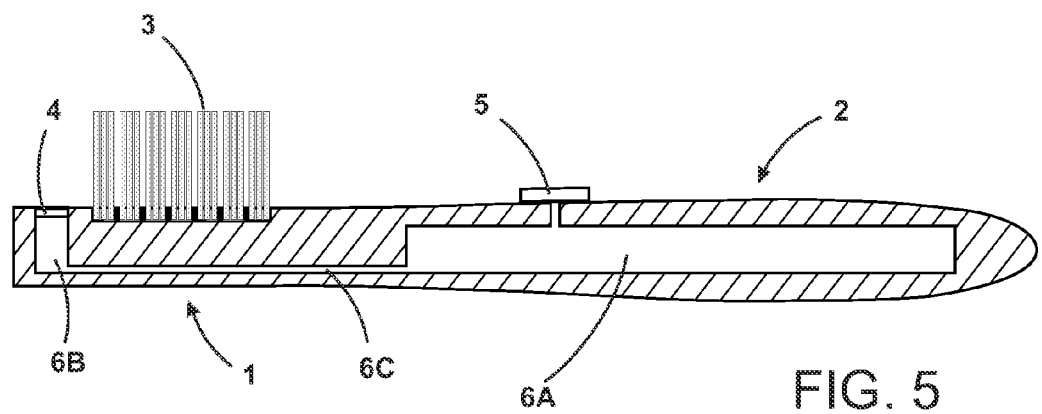
FIG. 5 is a cross-sectional side view of the toothbrush with camera of FIG. 3.

FIGS. 3, 4 and 5 show a toothbrush with camera of the invention. The toothbrush includes a head 1 that is attached to a handle 2 used for holding the toothbrush. The head 1 and the handle 2 of the toothbrush can be of plastic or of any other permissible material. The head 1 has tufts of bristles 3 arranged in rows. The tufts of bristles 3 can be of nylon or of any other permissible material. The bristles 3 are used to clean the teeth. The handle 2 has a hollow recess 6A. A camera 4 is placed in a hollow recess 6B in the head 1 of the toothbrush and is connected to other parts of the camera assembly placed in the recess 6A of the handle 2 through a passage 6C. The camera 4 is operated by a switch 5 on the handle 2. The camera 4 can comprise a lens and an image sensor (such as a charge coupled device—CCD) coupled to an image processor of a printed circuit board. It can be of any suitable size, shape and construction. The camera 4 can comprise a wireless image transmitter for transmitting camera images to a display unit that is not hardwired to the camera. Any suitable type of wireless image transmitter can be used and the transmitter can be located within the handle 2 and hardwired to the camera. The camera 4 can be used to see the teeth before, during and after brushing on a display unit such as a display monitor in the mirror of a bathroom. The images can also be seen on hand held devices such as Personal Digital Assistants (PDA), hand held televisions, data/video-enabled cellular telephones, and other hand held wired or wireless video-enabled devices and on computer monitors. Although PDAs may be connected to a desktop personal computer or other PDAs via infrared, blue tooth, direct wire, or wireless communication links, PDAs and similar hand held devices can be linked to remote networks such as the Internet, or local wireless resources, such as RF broadcasts, through available wireless communications techniques. The recorded images and videos can be sent anywhere in the world through the internet for consulting health care professionals. The camera 4 can comprise other components such as a power supply (e.g. a rechargeable lithium battery), Typically, these are incorporated into the handle 2 of the toothbrush. The battery can be charged by induction charging.

Figure 6:
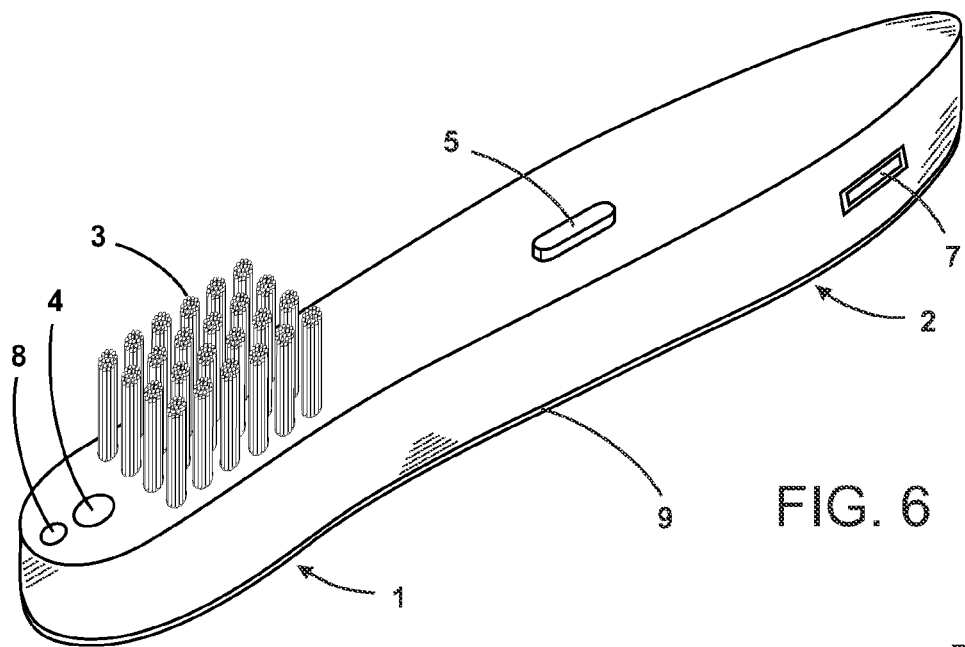
FIG. 6 is a perspective view of another embodiment of a toothbrush with camera according to the present invention showing a light source and a cable port for data transfer.
Figure 7:
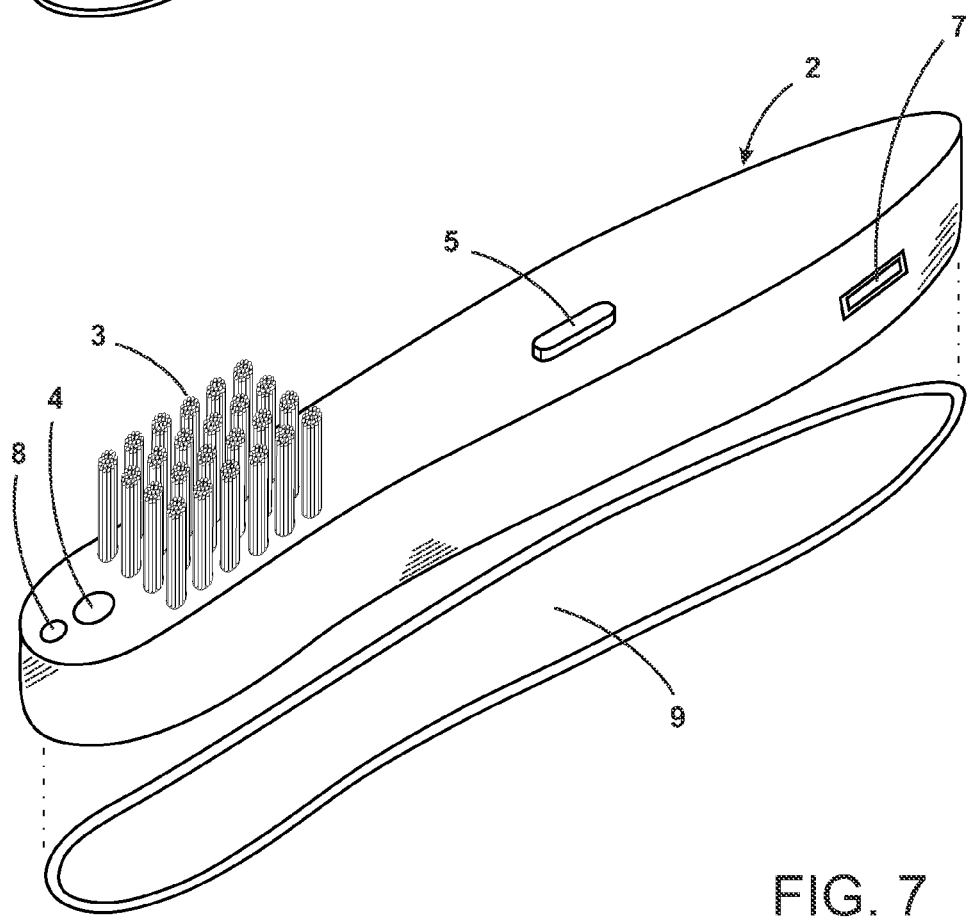
FIG. 7 is an exploded view of the toothbrush with camera of FIG. 6 with the cover in open position.

FIGS. 6 and 7 show another embodiment of toothbrush with camera of the invention wherein the head 1 contains a light source 8 placed near the camera 4 to illuminate the area captured by the camera 4. Any suitable type of light source can be used. Preferably, the light source 8 comprises at least one light emitting diode (LED). The handle 2 has a data transfer port 7 to connect the toothbrush to a display unit with a data transfer cable such as a USB cable that can also charge the battery.

Figure 8:
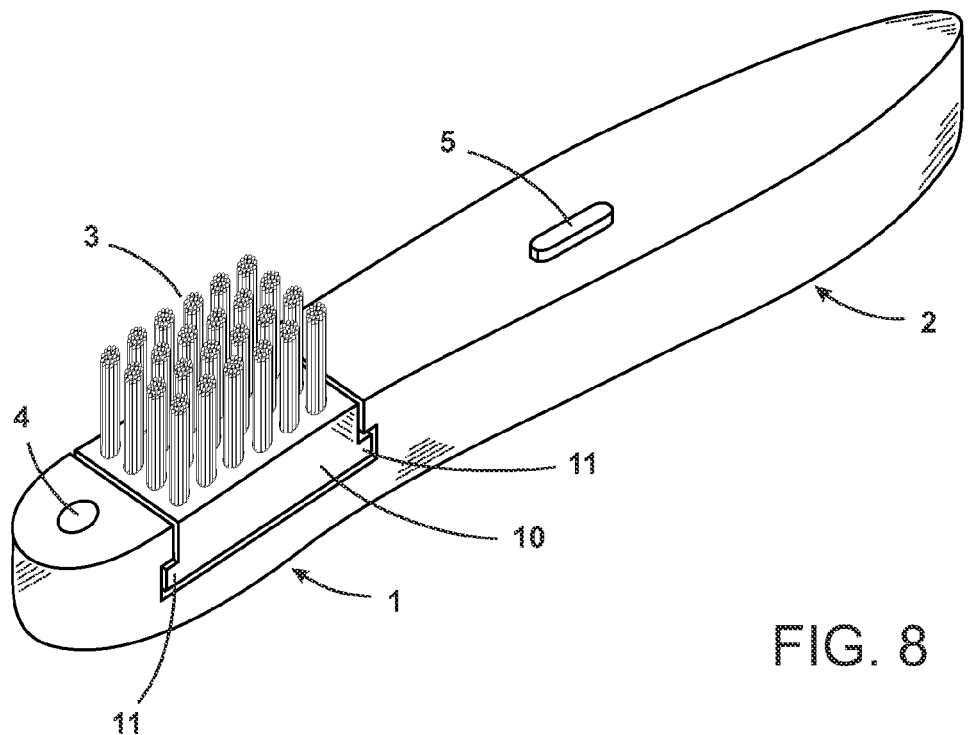
FIG. 8 is a perspective view another embodiment of a toothbrush with camera according to the present invention.
Figure 9:
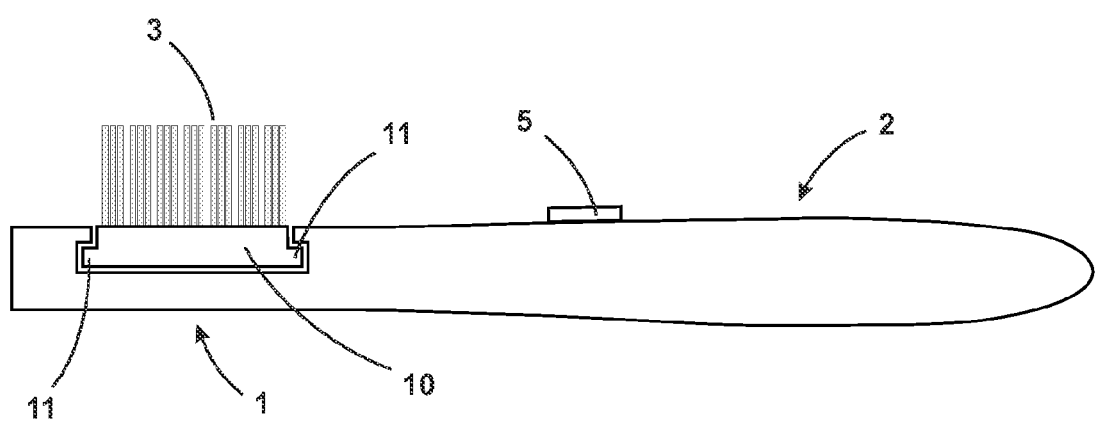
FIG. 9 is a side view of the toothbrush with camera of FIG. 8.
Figure 10:
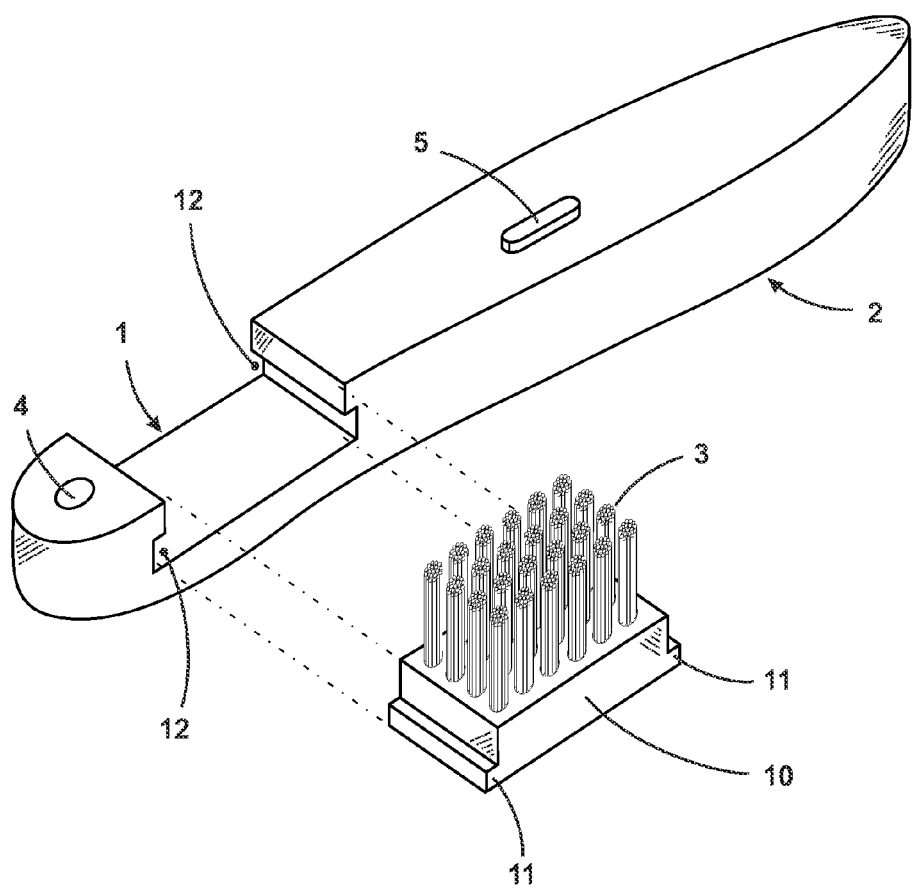
FIG. 10 is an exploded view of the toothbrush with camera of FIG. 8 showing the brush head in detached position.
Figure 11:
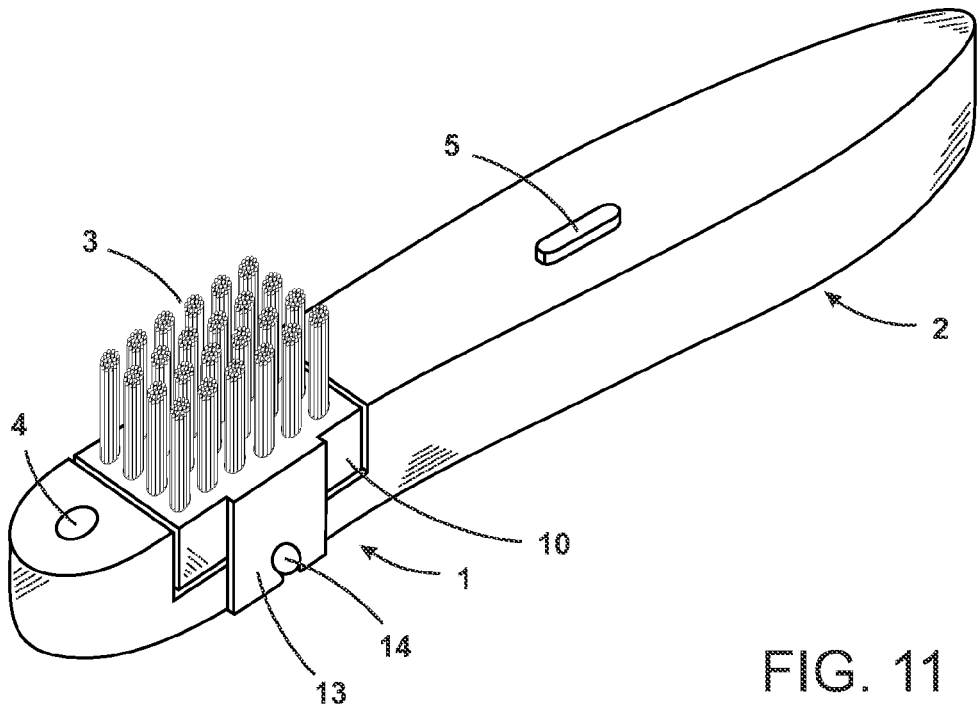
FIG. 11 is a perspective view another embodiment of a toothbrush with camera according to the present invention.
Figure 12:
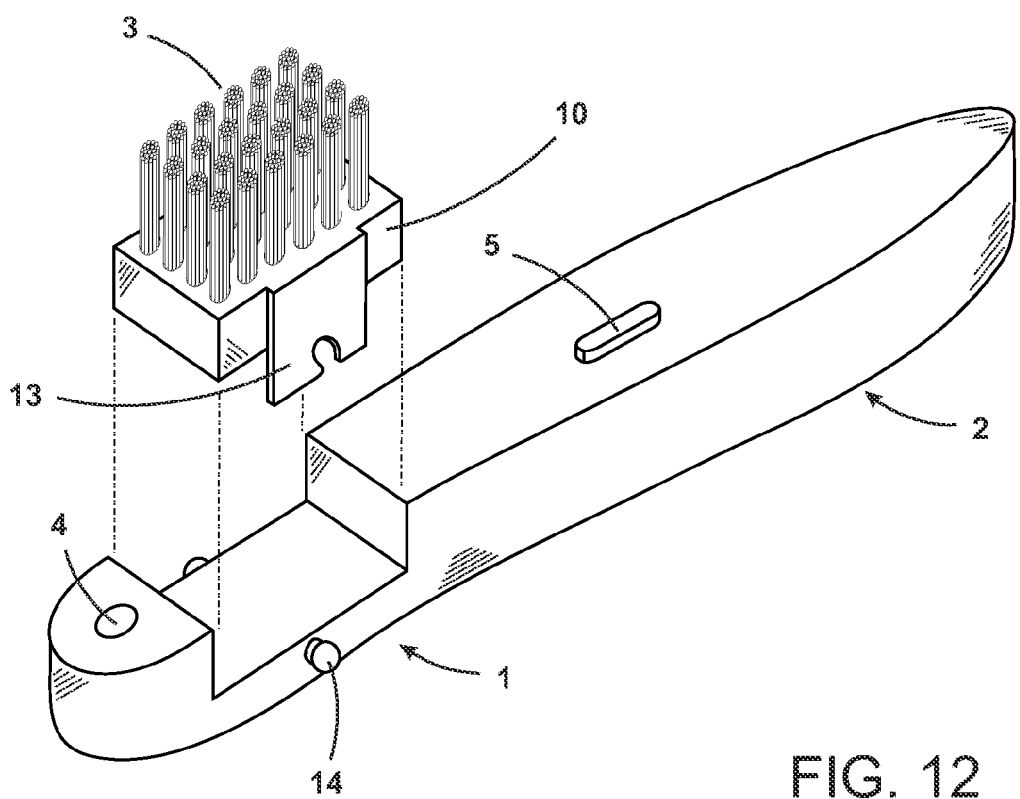
FIG. 12 is an exploded view of the toothbrush with camera of FIG. 11 showing the brush head in detached position.
Figure 13:
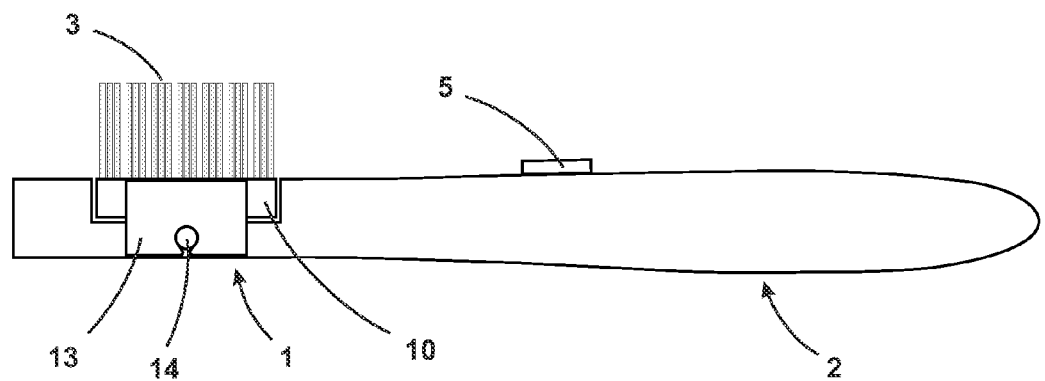
FIG. 13 is a side view of the toothbrush with camera of FIG. 11.
Figure 14:
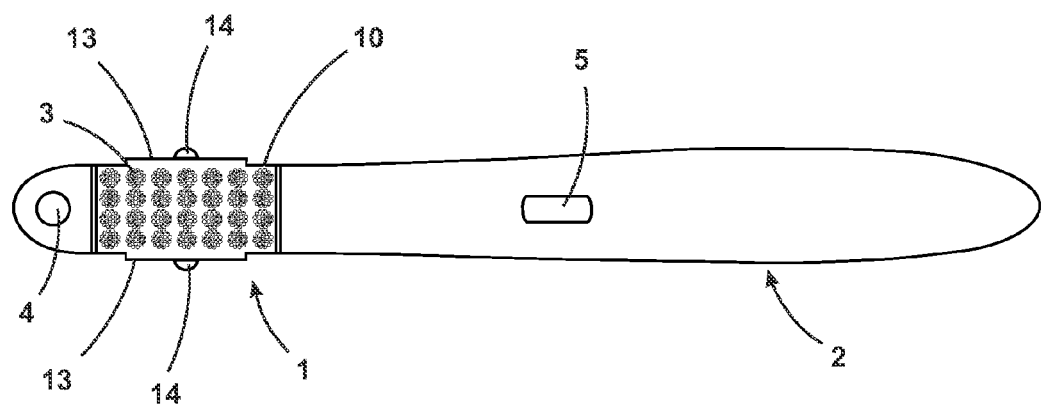
FIG. 14 is a top view of the toothbrush with camera of FIG. 11.

FIGS. 8, 9 and 10 show another embodiment of toothbrush with camera of the invention wherein the bristles are contained within a detachable section 10 of the head 1. Projections 11 of the detachable section 10 fit into cut out sections 12 of the brush head 1 when inserted sideways. This can allow changing of the bristles 3 after they get spoiled due to use, without changing the whole toothbrush with camera. It can also allow different users to use the toothbrush with camera after changing the bristles taking due measures to clean the head with camera.

FIGS. 11, 12, 13 and 14 show another embodiment of toothbrush with camera of the invention wherein the bristles 3 are contained within a detachable section 10 of the head 1 having extensions 13 that fit into projections 14 on either side of the head 1. The detachable section 10 can be pulled up vertically to change the bristles 3.

Figure 15:
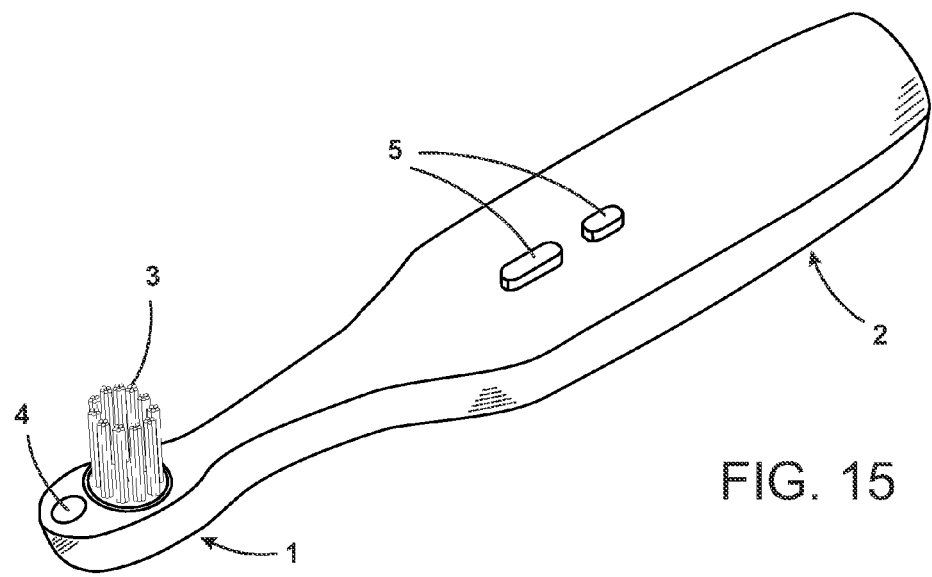
FIG. 15 is a perspective view of one embodiment of a motorised toothbrush with camera according to the present invention.
Figure 16:
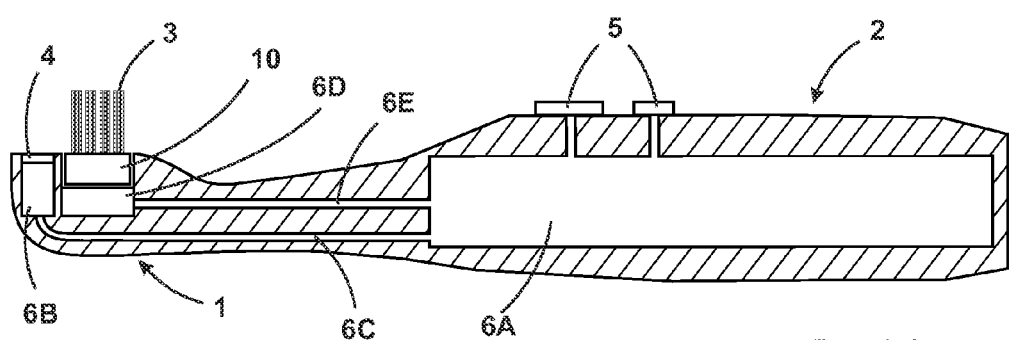
FIG. 16 is a cross-sectional side view of the toothbrush with camera of FIG. 15.
Figure 17:
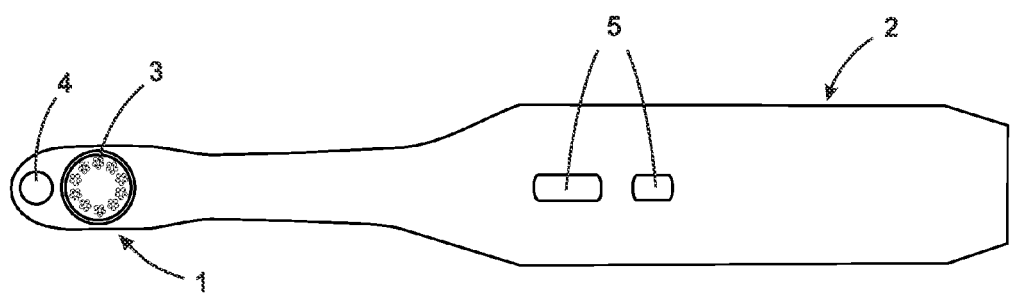
FIG. 17 is a top view of the toothbrush with camera of FIG. 15.

FIGS. 15, 16 and 17 show a motorised toothbrush with camera of the invention. The toothbrush includes a head 1 that is attached to a handle 2 used for holding the toothbrush. The head 1 has tufts of bristles 3 arranged in a circular manner on a movable base section 10 that rotates or oscillates in a semicircle when switched on. The handle 2 has a hollow recess 6A. A camera 4 is placed in a hollow recess 6B in the head 1 of the toothbrush and is connected to other parts of the camera assembly placed in the recess 6A of the handle 2 through a passage 6C. A motor assembly is placed in a recess 6D of the head 1 and is connected to its other parts placed in the recess 6A of the handle 2 through a passage 6E. The base section 10 is connected to a part of the motor assembly (not shown in Figure) placed in recess 6D. The camera 4 and the movable base section 10 are operated by switches 5 on the handle 2.

Figure 18:
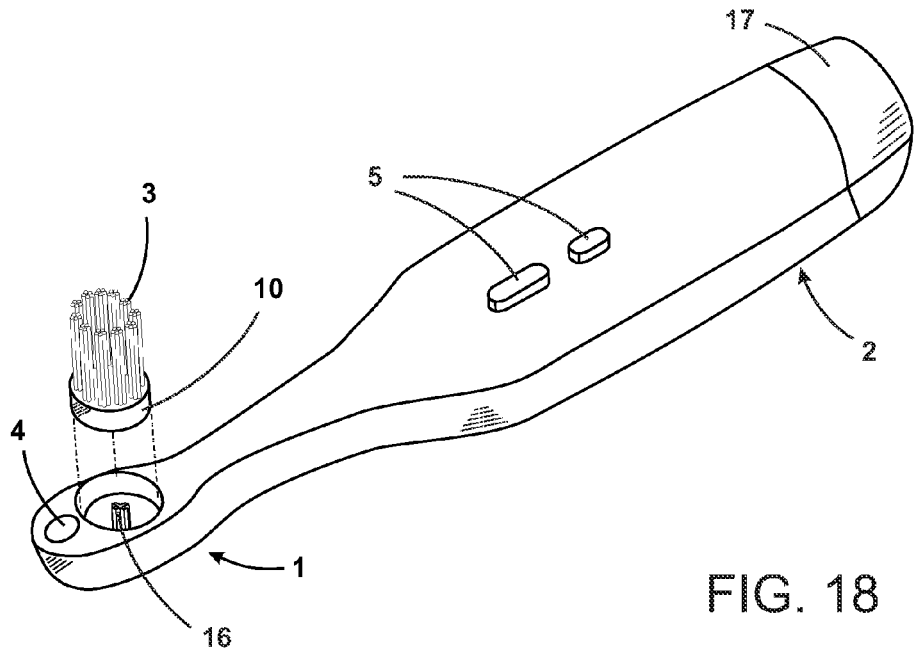
FIG. 18 is an exploded view of another embodiment of a motorised toothbrush with camera according to the present invention showing the brush head in detached position.
Figure 19:
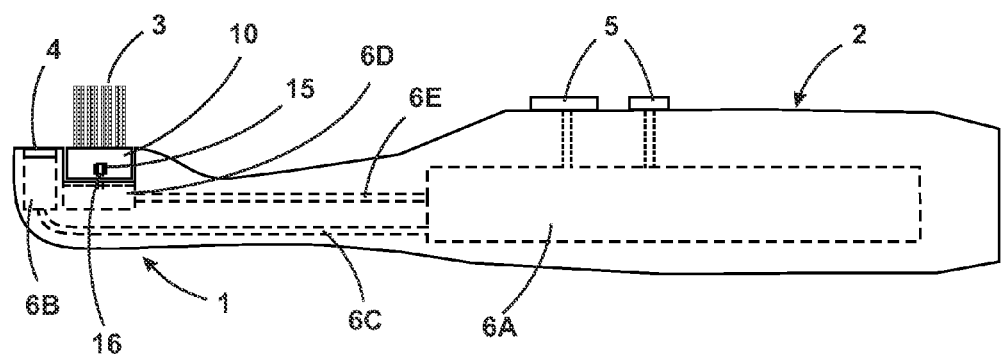
FIG. 19 is a side view of the toothbrush with camera of FIG. 18.

FIGS. 18, and 19 show another embodiment of the motorised toothbrush with camera of the invention wherein the base section 10 containing bristles 3 is detachable. A projection 16 of a motor assembly fits into a recess 15 in the bristle-head section 10.

Figure 20:
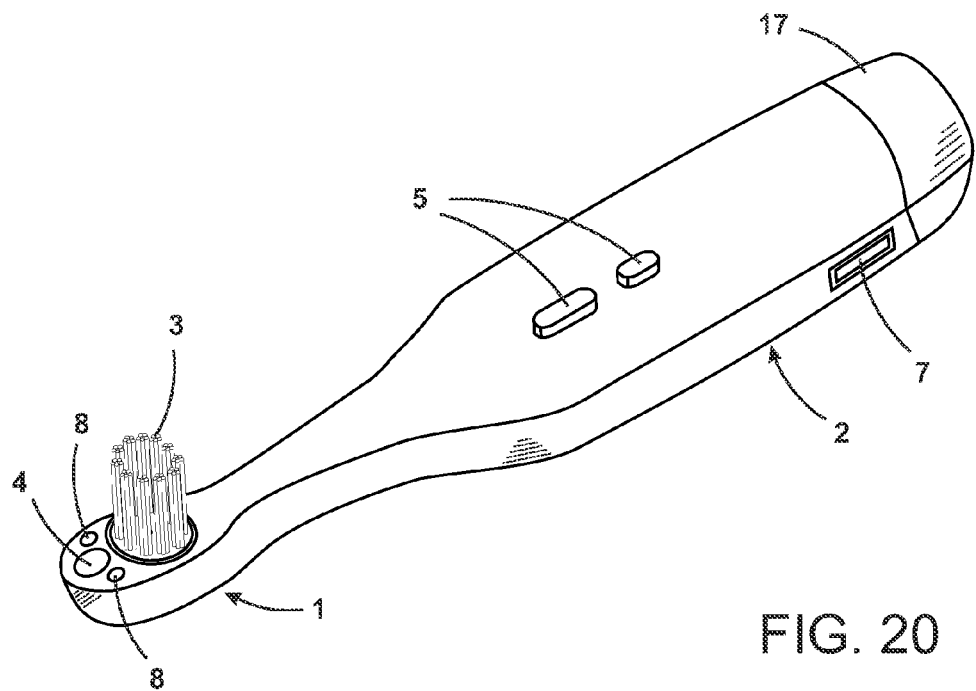
FIG. 20 is a perspective view of another embodiment of a motorised toothbrush with camera according to the present invention showing a light source and a data cable port for data transfer.
Figure 21:
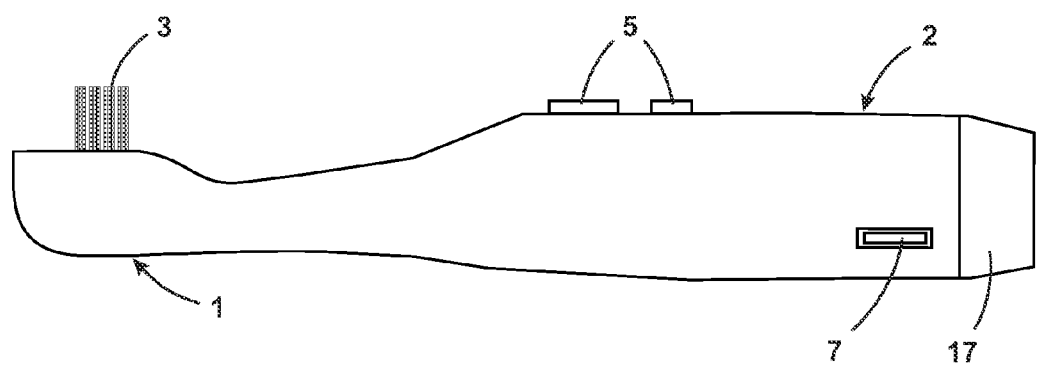
FIG. 21 is a side view of the toothbrush with camera of FIG. 20.
Figure 22:
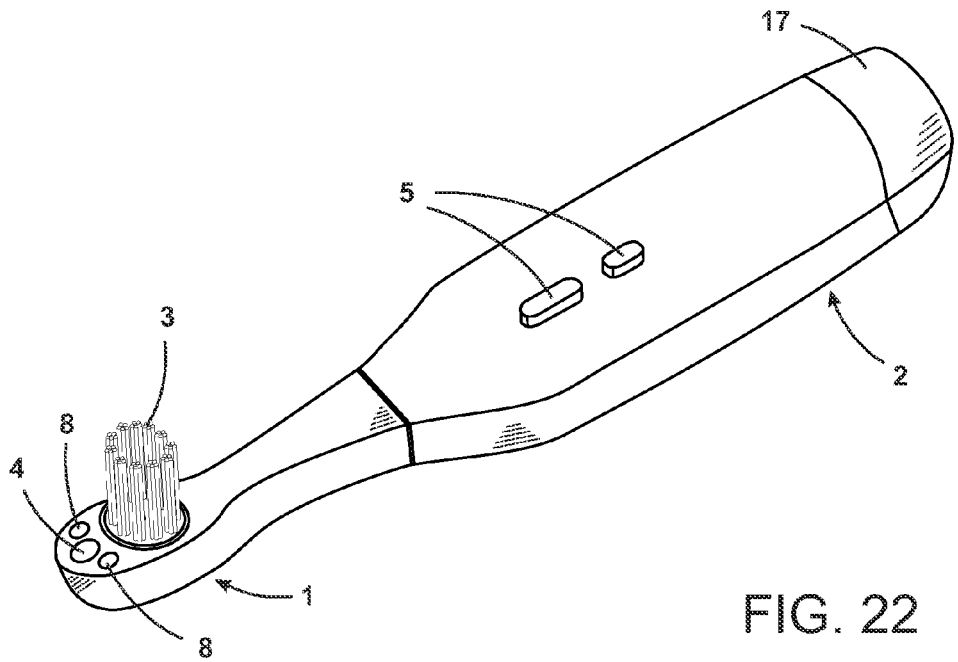
FIG. 22 is a perspective view of another embodiment of a motorised toothbrush with camera according to the present invention.
Figure 23:
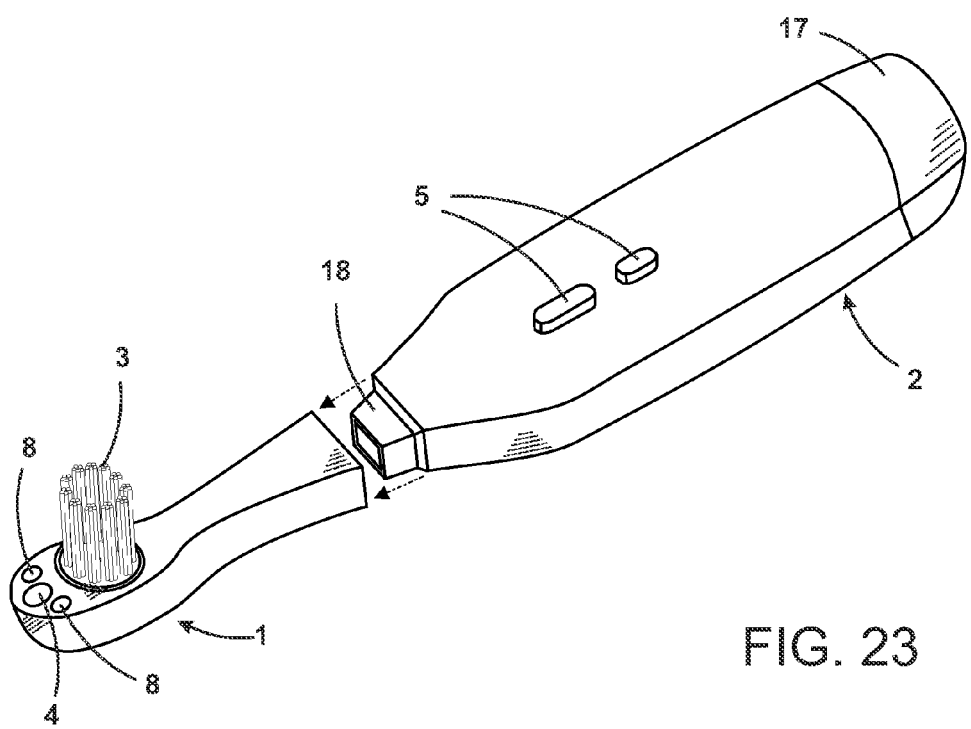
FIG. 23 is an exploded view of the toothbrush with camera of FIG. 22 showing the brush head in detached position.
Figure 24:
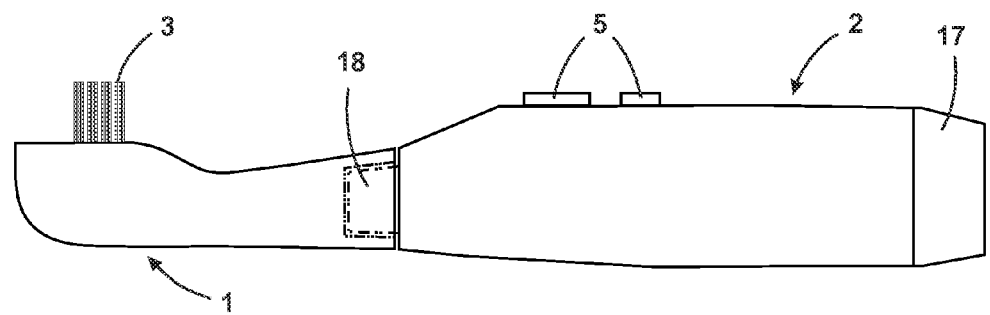
FIG. 24 is a side view of the toothbrush with camera of FIG. 22.
Figure 25:
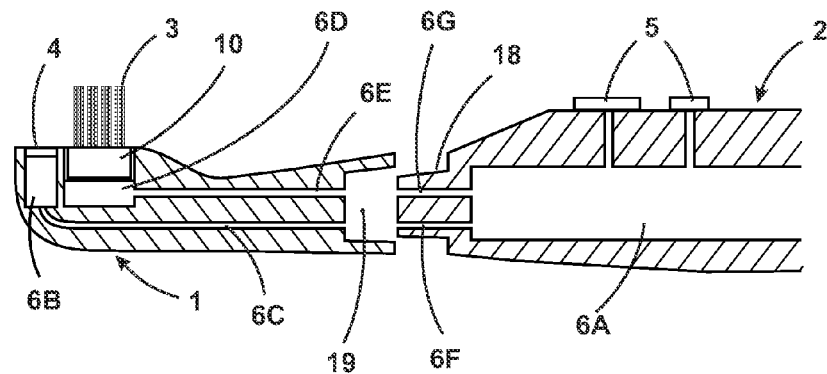
FIG. 25 is a cross-sectional side view of the toothbrush with camera of FIG. 22.
Figure 26:
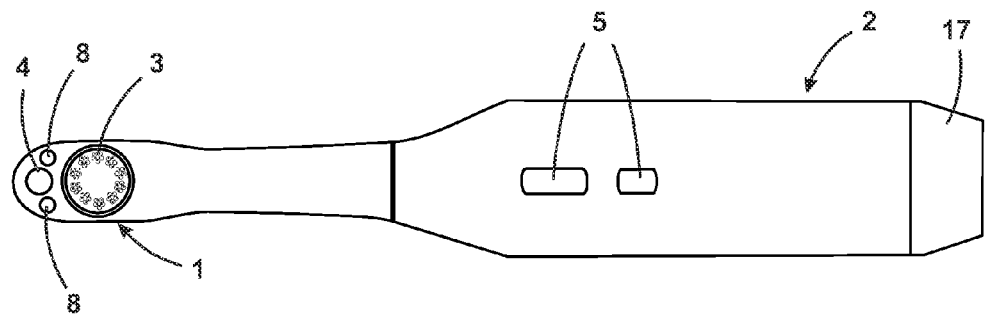
FIG. 26 is a top view of the toothbrush with camera of FIG. 22.
Figure 27:
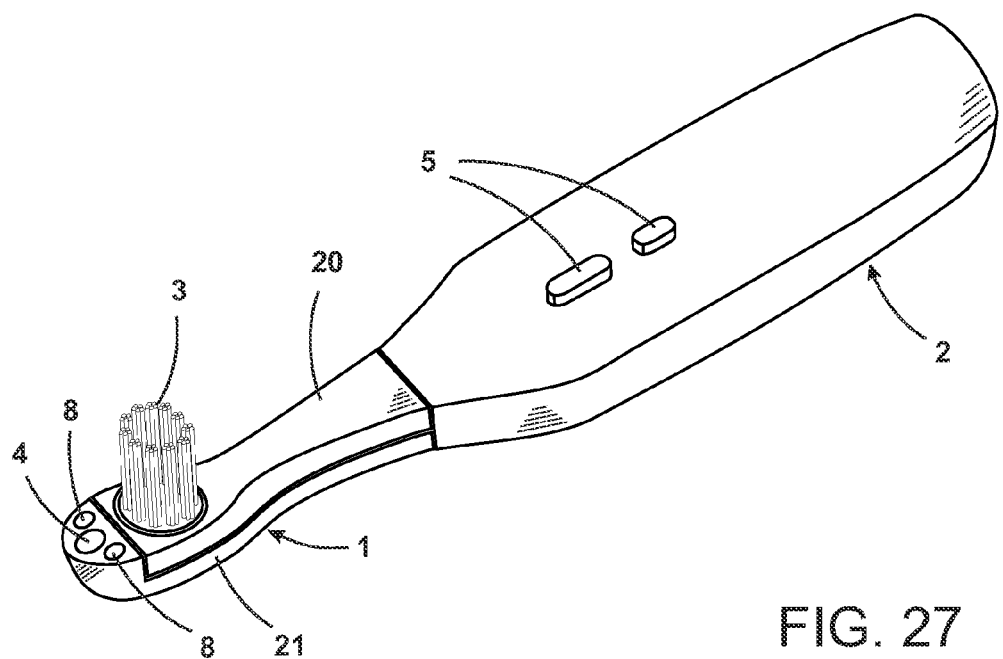
FIG. 27 is a perspective view of another embodiment of a motorised toothbrush with camera according to the present invention.
Figure 28:
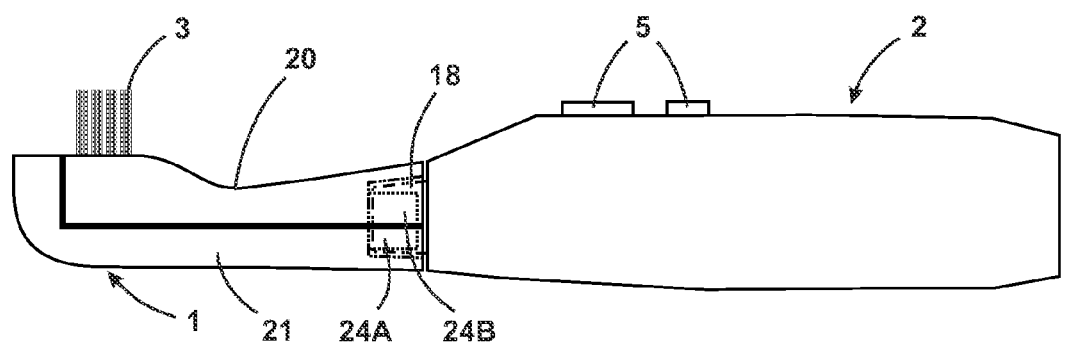
FIG. 28 is a side view of the toothbrush with camera of FIG. 27.
Figure 29:
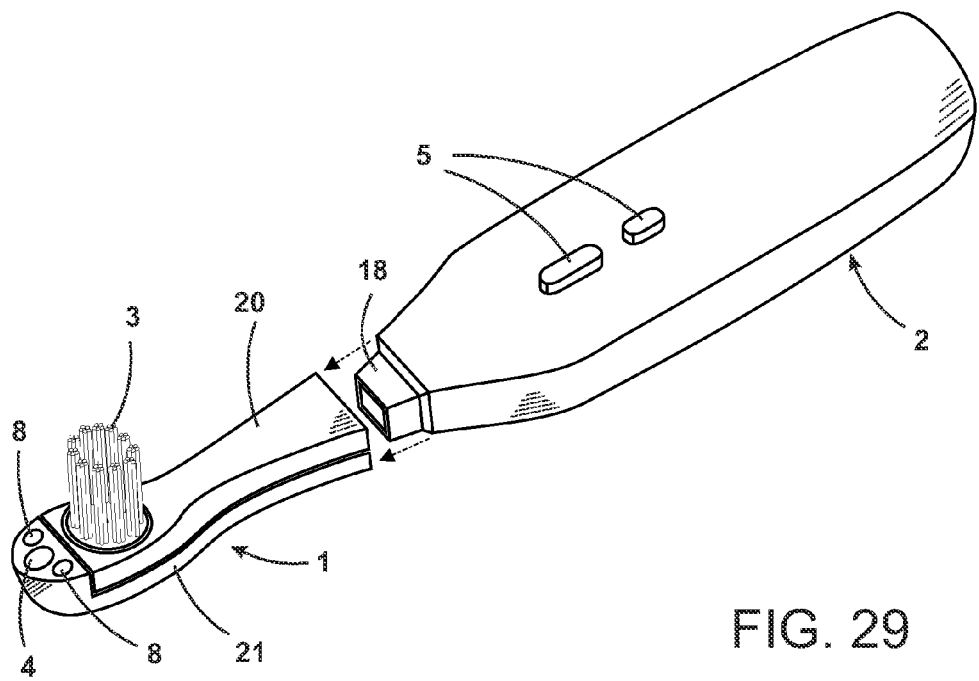
FIG. 29 is a partly exploded view of the toothbrush with camera of FIG. 27 showing the brush head and the camera section detached from the handle.
Figure 30:
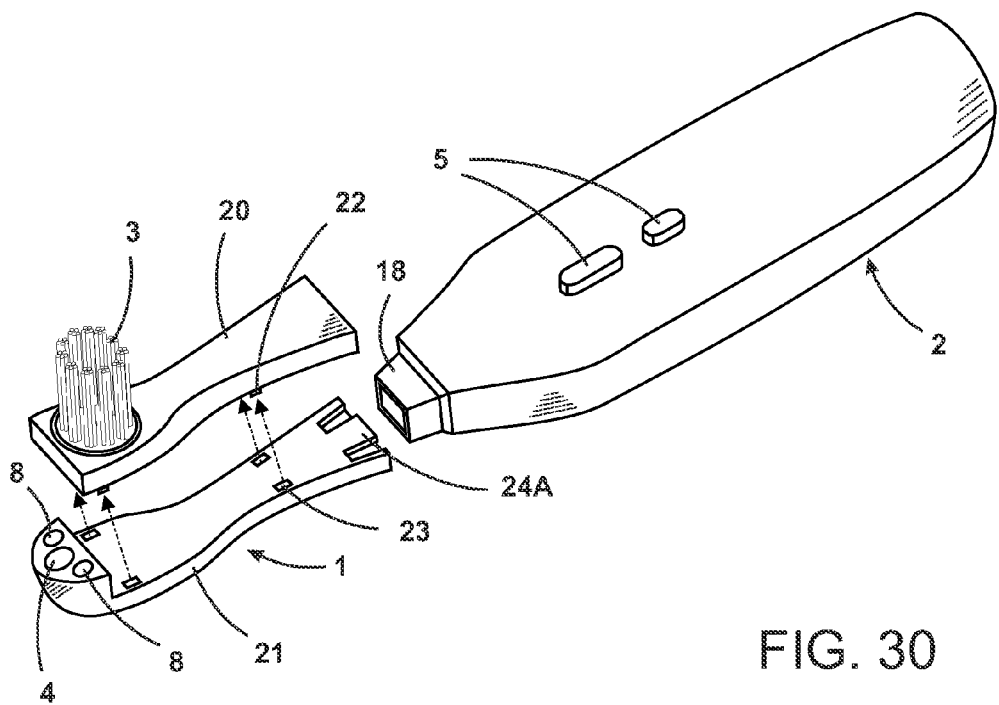
FIG. 30 is a fully exploded view of the toothbrush with camera of FIG. 27 showing the brush head and the camera section detached from each other and the handle.
Figure 31:
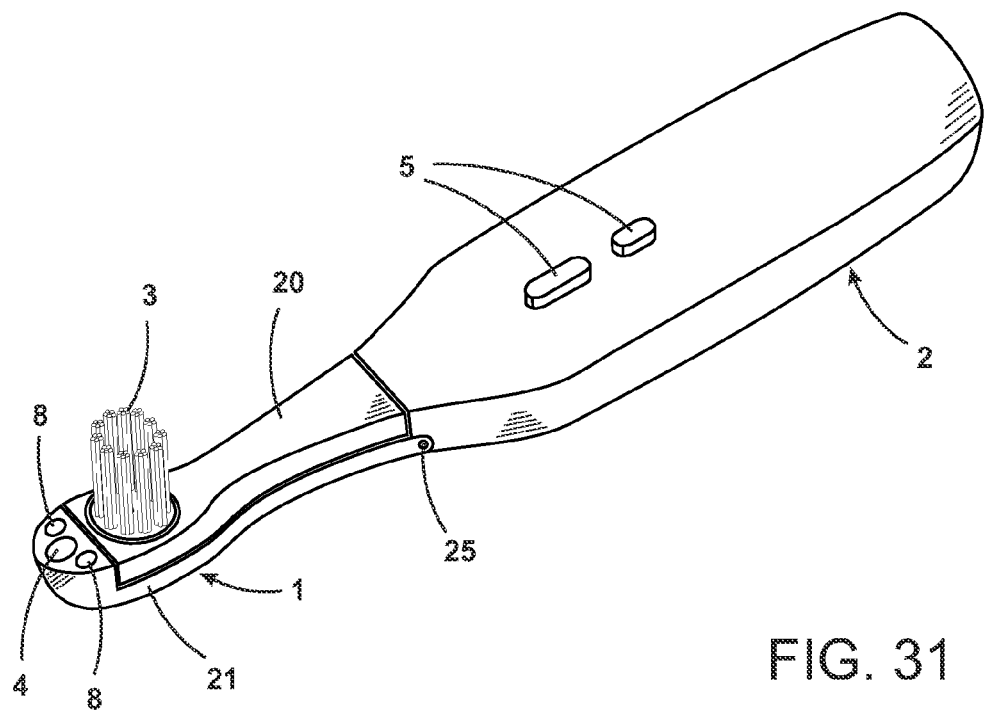
FIG. 31 is a perspective view of another embodiment of a motorised toothbrush with camera according to the present invention.
Figure 32:
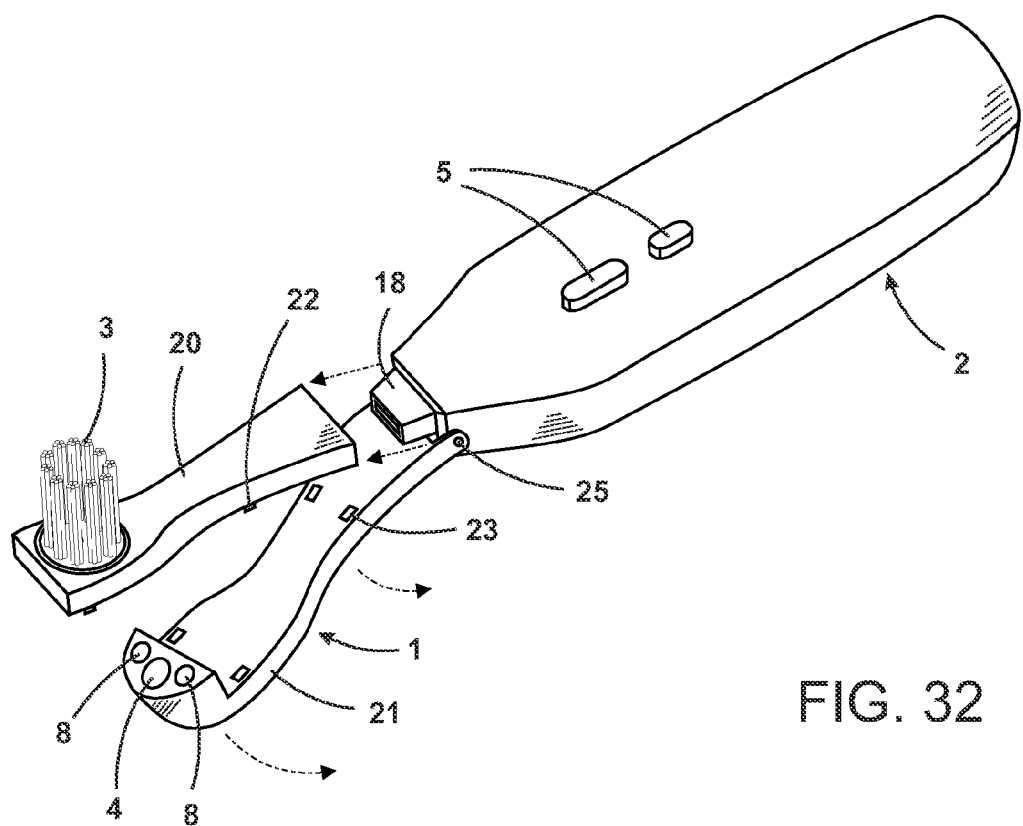
FIG. 32 is an exploded view of the toothbrush with camera of FIG. 31 showing the camera section moved around a pivot and the brush head detached from the handle and the camera section.
Figure 33:
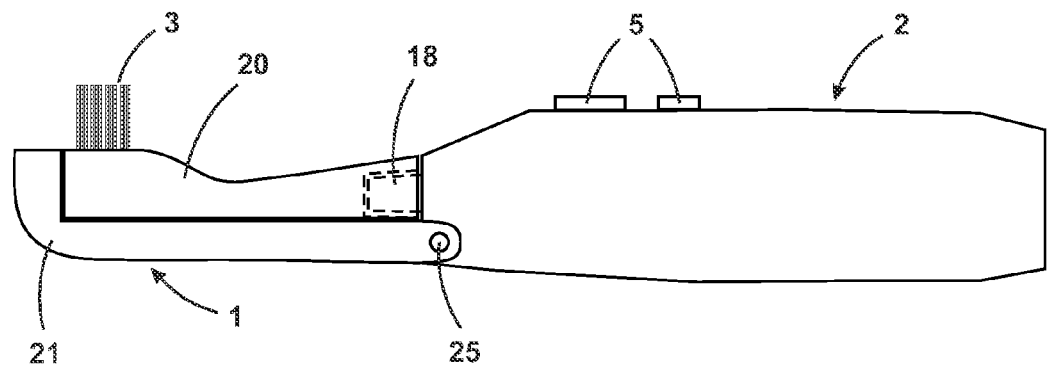
FIG. 33 is a side view of the toothbrush with camera of FIG. 31.
Figure 34:
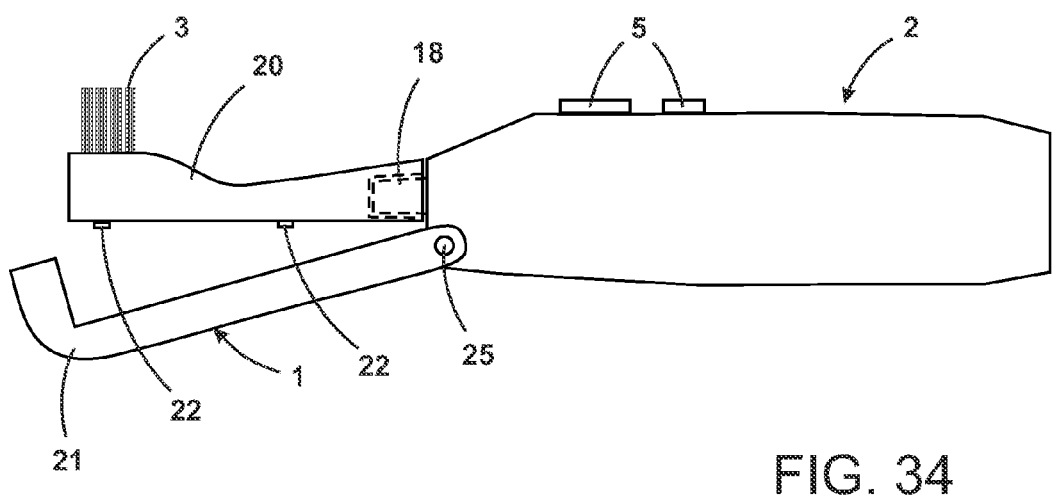
FIG. 34 is a side view of the toothbrush with camera of FIG. 31 showing the camera section in open position.

FIGS. 20, and 21 show another embodiment of the motorised toothbrush with camera of the invention wherein two light sources 8 are placed in the brush head 1 near camera 4. The handle 2 has a data transfer port 7 to connect the toothbrush to a display unit with a data transfer cable such as a USB cable that can also charge the battery. The handle 2 has a cover 17 to access the inside of the tooth brush.

FIGS. 22, 23, 24, 25 and 26 show another embodiment of the motorised toothbrush with camera of the invention wherein the head 1 can be separated from the handle 2 to replace the bristles 3. A projection 18 of the handle 2 fits into a recess 19 of the head 1. A camera 4 is placed in a hollow recess 6B in the head 1 of the toothbrush and is connected to other parts of the camera assembly placed in the recess 6A of the handle 2 through passages 6C in the head 1 and 6F in the projection 18 of the handle 2. A motor assembly is placed in a recess 6D of the head 1 and is connected to its other parts placed in the recess 6A of the handle 2 through passages 6E in the head 1 and 6G in the projection 18 of the handle 2. The bristle-head section 10 is connected to a part of the motor assembly (not shown in Figure) placed in recess 6D. The camera 4 and the movable bristle-head section 10 are operated by switches 5 on the handle 2.

FIGS. 27, 28, 29 and 30 show another embodiment of the motorised toothbrush with camera of the invention wherein the head 1 can be separated from the handle 2 to replace the bristles 3. The head 1 of the toothbrush has two parts, the bristle-head section 20 and the camera-head section 21. The bristle-head section 20 can separate from the camera-head section 21 after the head 1 is separated from the handle 2. The bristle-head section can be replaced when the bristles get spoiled, without changing the camera-head section 21. Projections 22 in the bristle-head section 20 fit into depressions 23 in the camera-head section 21 when the two sections are pressed together. A projection 24A in the camera-head section 21 and a projection 24B in the bristle-head section 20 fit into a projection 18 of the head 2.

FIGS. 31, 32, 33 and 34 show another embodiment of the motorised toothbrush with camera of the invention wherein the camera-head section 21 can rotate around a pivot 25 in the handle 2 to move into an open position so that the brush-head section 20 gets separated from the camera-head section 21. Then the brush-head section 20 can be detached from the handle 2 for a replacement. Projections 22 in the brush head-section 20 fit into depressions 23 in the camera head section 21 to lock the two parts when the brush head section 20 is fitted into projection 18 of the handle 2 and the camera head section 21 is moved into close position. The camera head section 21 remains connected to the camera assembly housed in the recess of the handle through flexible wire connectors.

Although the description above contains many specificities, these should not be construed as limiting the scope of the invention but as merely providing illustrations of some of the presently preferred embodiments of this invention. For example, the head and the handle of the toothbrush can have various shapes like round, square, oval, triangular, rhomboid, trapezoid etc. The imaging device being camera can be replaced with any other imaging device having similar functions as those of a camera. The imaging device can have two or mare cameras spaced apart to capture 3-D images. The camera lens can be placed anywhere on the toothbrush head. The camera can have auto-focus facility. Preferably the toothbrush with camera has three LEDs mounted within the head. The bristles on the motorised toothbrush may not be placed in a circle. The bristles may move in a forward-backward direction rather than in a circular motion. The toothbrush with camera would be made waterproof to prevent the camera from getting spoilt. Although the edges of the toothbrush are sharp in the drawings, they would be smoothened in the manufactured brushes to make them comfortable to the patients.

What is claimed is:

1. A toothbrush with an imaging device being camera comprising: a head containing bristles for cleaning teeth connected to a handle and the head containing a camera connected to a camera assembly contained within the handle, the bristles of the head disposed within a detachable section of the head and disposed substantially parallel to the camera, that is selectively removable from the head, while the camera is contained in a section of the head that is selectively pivotable from the handle and selectively pivotable away from the detachable section of the head.

2. The toothbrush with an imaging device being camera defined in claim 1, wherein said camera contains a wireless transmitter for transmitting camera images to an image display that is independent of said toothbrush with camera.

3. The toothbrush with an imaging device being camera defined in claim 1, wherein said handle contains a data transfer port connected to said camera for transferring camera images through a data cable to an image display that is independent of said toothbrush with camera.

4. The toothbrush with an imaging device being camera defined in claim 1, wherein said detachable section of said head has projections on either side to fit into cut-out areas in said head when pushed into said head sideways.

5. The toothbrush with an imaging device being camera defined in claim 4, wherein said head contains at least one source of light and said camera contains a wireless transmitter for transmitting camera images to an image display that is independent of said toothbrush with camera.

6. The toothbrush with an imaging device being camera defined in claim 4, wherein said detachable section of said head has extensions with notches on either side to fit into projections on either side of said head when pushed into said head from above.

7. The toothbrush with an imaging device being camera defined in claim 6, wherein said head contains at least one source of light and said camera contains a wireless transmitter for transmitting camera images to an image display that is independent of said toothbrush with camera.

8. A toothbrush with an imaging device being camera comprising: a head connected to a handle, said head containing bristles for cleaning teeth, said bristles mounted on a movable base connected to a motor assembly contained within said handle; and said head also containing a camera connected to a camera assembly contained within said handle said head having two sections, one section of said head containing said bristles, that can be detached from said handle via said movable base and said other section of said head having said camera, that can selectively rotate around a pivot fixed to said handle to move away from said section containing said movable base containing said bristles and to pivot from said handle.

9. The toothbrush with an imaging device being camera defined in claim 8, wherein said camera contains a wireless transmitter for transmitting camera images to an image display that is independent of said toothbrush with camera.

10. The toothbrush with an imaging device being camera defined in claim 8, wherein said handle contains a data transfer port connected to said camera for transferring camera images through a data cable to an image display that is independent of said toothbrush with camera.

11. The toothbrush with an imaging device being camera defined in claim 8 wherein said movable base containing said bristles is detachable from said other section of said head having said camera.

12. The toothbrush with an imaging device being camera defined in claim 8 wherein said head is detachable from said handle.

13. A toothbrush comprising:
a selectively removable bristle head connected to a handle, the bristle head including bristles extending from the handle in a first bristle direction;
a camera assembly selectively connected to the selectively removable bristle head and pivotably connected to the handle, the camera assembly including a camera disposed along the handle and arranged to capture images in the first bristle direction during operation of the toothbrush.

14. A toothbrush according to claim 13, further comprising at least one led disposed in the handle and arranged to illuminate in the first bristle direction.

15. A toothbrush according to claim 13, further comprising a data transfer port connected to said camera for transferring camera images through a data cable to an image display that is independent of the toothbrush.

16. A toothbrush according to claim 13, further comprising a wireless transmitter disposed in the handle for transmitting camera images to an image display that is independent of the toothbrush with camera, and wherein the camera is adapted and constructed to capture images in the first bristle direction before, during, and after operation of the toothbrush.

\* \* \* \* \*